(12) United States Patent
Truitt et al.

(10) Patent No.: US 8,074,647 B2
(45) Date of Patent: *Dec. 13, 2011

(54) IMPELLER AND A PRESSURE SUPPORT SYSTEM AND METHOD USING SUCH A METHOD

(75) Inventors: Patrick W Truitt, Murrysville, PA (US); Kay Herbert, Winthrop, MA (US)

(73) Assignee: RIC Investments LLC, Wilmington, DE (US)

( * ) Notice: Subject to any disclaimer, the term of this patent is extended or adjusted under 35 U.S.C. 154(b) by 2231 days.

This patent is subject to a terminal disclaimer.

(21) Appl. No.: 10/623,336

(22) Filed: Jul. 18, 2003

(65) Prior Publication Data

US 2004/0071552 A1    Apr. 15, 2004

Related U.S. Application Data

(62) Division of application No. 09/883,035, filed on Jun. 15, 2001, now Pat. No. 6,622,724.

(60) Provisional application No. 60/212,245, filed on Jun. 19, 2000.

(51) Int. Cl.
*A61M 16/00*  (2006.01)

(52) U.S. Cl. .......... 128/204.21; 128/204.18; 128/200.24

(58) Field of Classification Search ............. 128/204.18, 128/204.21, 204.23, 204.25; 415/200, 206, 415/217.1, 228, 911; 416/132 A, 186 R, 416/130, 183, 185; 417/407; 123/565
See application file for complete search history.

(56) References Cited

U.S. PATENT DOCUMENTS

| | | | | |
|---|---|---|---|---|
| 3,751,179 A | * | 8/1973 | Wassmann | 415/228 |
| 3,904,308 A | * | 9/1975 | Ribaud | 415/143 |
| 3,915,591 A | | 10/1975 | Aiki et al. | |
| 4,502,837 A | * | 3/1985 | Blair et al. | 415/198.1 |
| 4,602,653 A | * | 7/1986 | Ruiz-Vela et al. | 137/88 |
| 4,653,976 A | * | 3/1987 | Blair et al. | 415/198.1 |
| 4,759,690 A | | 7/1988 | Deschamps et al. | |
| 4,957,107 A | * | 9/1990 | Sipin | 128/204.21 |
| 4,981,414 A | * | 1/1991 | Sheets | 415/149.1 |
| 5,065,756 A | * | 11/1991 | Rapoport | 128/204.18 |
| 5,066,195 A | * | 11/1991 | Dobrzynski | 416/200 R |
| 5,152,661 A | * | 10/1992 | Sheets | 415/84 |
| 5,224,823 A | * | 7/1993 | Cordts | 415/206 |
| 5,452,714 A | * | 9/1995 | Anderson et al. | 128/205.11 |
| 5,597,289 A | * | 1/1997 | Thut | 415/200 |
| 5,695,318 A | * | 12/1997 | Harmsen | 415/218.1 |
| 5,741,123 A | * | 4/1998 | Pauly | 417/407 |
| 5,868,133 A | * | 2/1999 | DeVries et al. | 128/204.21 |
| 5,875,783 A | | 3/1999 | Kullik et al. | |
| 6,085,747 A | * | 7/2000 | Axe et al. | 128/204.23 |
| 6,224,335 B1 | * | 5/2001 | Parisi et al. | 415/206 |
| 6,543,449 B1 | * | 4/2003 | Woodring et al. | 128/204.18 |
| 6,622,724 B1 | * | 9/2003 | Truitt et al. | 128/204.18 |

FOREIGN PATENT DOCUMENTS

WO    WO99/13932    * 3/1999

* cited by examiner

*Primary Examiner* — Justine Yu
*Assistant Examiner* — Annette Dixon
(74) *Attorney, Agent, or Firm* — Michael W. Haas

(57) ABSTRACT

An impeller, a pressure generator using such an impeller, and a pressure support system and method using such a pressure generator to deliver a flow of breathing gas to a patient is disclosed. The impeller enables a pressure of a flow of breathing gas delivered by a pressure support system to a patient to remain substantially constant despite variations of the output flow rate. The impeller includes a plurality of impeller blades disposed on a face of the impeller body with an inlet area between each pair of adjacent blades being substantially equal a corresponding outlet area for each pair of adjacent blades.

12 Claims, 8 Drawing Sheets

IMPELLER AND A PRESSURE SUPPORT SYSTEM AND METHOD USING SUCH A METHOD

CROSS-REFERENCE TO RELATED APPLICATIONS

The present invention claims priority under 35 U.S.C. §120 as a Divisional of U.S. application Ser. No. 09/883,035 filed Jun. 15, 2001, which claims priority under 35 U.S.C. §119(e) from U.S. provisional patent application No. 60/212,245 filed Jun. 19, 2000.

BACKGROUND OF THE INVENTION

1. Field of the Invention

The present invention pertains to an impeller, a pressure generator using such an impeller, and a pressure support system and method using such a pressure generator to deliver a flow of breathing gas to a patient, and, in particular, to an improved impeller that enables a pressure of a flow of breathing gas delivered by a pressure support system to a patient to remain substantially constant despite variations of the output flow rate.

2. Description of the Related Art

Pressure support systems that provide a flow of gas to an airway of a patient at an elevated pressure to treat a medical disorder are well known. For example, it is known to use a continuous positive airway pressure (CPAP) device to supply a constant positive pressure to the airway of a patient throughout the patient's respiratory cycle to treat obstructive sleep apnea (OSA) as well as other cardiopulmonary disorders. An example of a CPAP device is the REMstar® and Solo® family of devices manufactured and distributed by Respironics, Inc. of Pittsburgh, Pa.

It is also known to provide a positive pressure therapy in which the pressure of gas delivered to the patient varies with the patient's breathing cycle. A conventional life support ventilator, such as the Esprit® Ventilator, also manufactured by Respironics, is an example of a pressure support system in which the pressure of gas delivered to the patient varies so as to replace or supplement the patient's own respiration. Another example of a pressure support device that provides "bi-level" pressure support in which a lower pressure is delivered during the patient's expiratory phase than during the inspiratory phase, is the BiPAP® family of devices manufactured and distributed by Respironics, Inc. It is further known to provide an auto-titration positive pressure therapy in which the pressure provided to the patient changes based on the detected conditions of the patient, such as whether the patient is snoring or experiencing an apnea, hypopnea or upper airway resistance. An example of a device that adjusts the pressure delivered to the patient based on whether or not the patient is snoring is the Virtuoso® CPAP family of devices manufactured and distributed by Respironics, Inc. An example of a pressure support device that actively tests the patient's airway to determine whether obstruction, complete or partial, could occur and adjusts the pressure output to avoid this result is the Tranquility® Auto CPAP device, also manufactured and distributed by Respironics, Inc.

In providing a respiratory therapy to a patient, a pressure support system, such as CPAP, ventilator, bi-level, or auto-titration pressure support device, typically delivers a flow of a breathing gas, such as air, oxygen, or an oxygen mixture, to an airway of the patient at a desired pressure, at least during a portion of the patient's respiratory cycle. A CPAP system, for example, delivers a constant pressure to the patient's airway throughout the patient's respiratory cycle. A typical pressure support system includes a source of gas, such as atmosphere, an oxygen tank or the like, or a combination thereof, a pressure generator with a pressure or flow control capability to generate and maintain a flow of breathing gas at the selected pressure, a patient circuit to deliver the flow of breathing gas to the patient, and a patient interface to communicate the flow of breathing gas with the patient's airway. The patient circuit typically is a flexible conduit having a patient interface device attached thereto. The patient interface is any device, such as a nasal/oral mask, nasal cannula, trachea tube, hood or the like, for communicating the flow of breathing gas with the patient's airway.

The pressure generator in conventional a pressure support system typically includes a motor driving a blower, which is an impeller within a housing, for placing the gas from the gas source under pressure relative to ambient atmosphere. In a conventional blower, the pressure output by the blower varies with the rate of flow in the patient circuit, assuming that the blower operates at a constant speed. For example, at a certain operating speed, the pressure in the patient circuit or patient interface decreases as the flow of gas in the patient circuit or at the patient interface increases. This occurs, for example, as the patient breathes into the patient circuit. For this reason, a conventional pressure support system typically includes a pressure/flow control system, which includes a sensor and a processor operating in a feedback fashion, to control and maintain the desired pressure or flow for the breathing gas delivered to the patient as the flow within the patient circuit fluctuates.

Various pressure/flow control techniques are known for controlling the flow of breathing gas output by the pressure generator and/or delivered to the patient so that the output pressure remains constant at the selected pressure despite variations in the flow of gas in the patient circuit or at the patient interface. In each of the conventional pressure/flow control techniques, either the pressure of gas in the patient circuit or at the patient interface, the flow of gas in the patient circuit, or a combination thereof, must be monitored, either directly or indirectly, for providing a feedback signal in the feedback pressure/flow control system.

In a first type of conventional pressure/flow control technique, during operation, the blower operates at substantially constant speed that is sufficient to deliver a pressure in excess of the selected pressure at to be delivered to the patient. The pressure output by the blower must be high enough above the selected pressure to be delivered to the patient's airway to allow the selected pressure to be delivered to the patient even if a pressure drop associated with an increase of flow occurs in the patient circuit. This pressure/flow technique also requires an exhaust valve to bleed off excess pressure or flow from the patient circuit, for example, when the flow in the patient circuit is relatively low. The amount of exhaust flow is controlled by the controller based on the feedback signals from the pressure and/or flow sensor to provide the selected pressure to the patient.

In a second type of conventional pressure/flow control technique, the motor in the blower does not operate at a constant speed, but is sped up or slowed down as needed to maintain the desired pressure. The motor speed is controlled by the controller based on the feedback signals from the pressure and/or flow sensor to provide the selected pressure to the patient. It is also known to use a combination of motor speed control and exhaust flow control to regulate the pressure or flow of breathing gas delivered to the patient.

These conventional types of pressure/flow control techniques, however, have certain drawbacks. In the exhaust flow control technique, bleeding off excessive pressure or flow requires the impeller to deliver more pressure than needed, which is inherently inefficient. In the motor speed control technique, cycling the motor speed is also inefficient and, due to the inertia of the impeller, does not allow for relatively rapid changes in the output pressure or flow. In addition, repeated cycling of the blower speed decreases the motor life as well as the efficiencies of the motor. It can be appreciated that either of these types of pressure control systems require a relatively expensive pressure and/or flow sensor to provide the feedback signal, as well as a relatively complicated pressure/flow control system that operates based on this feedback signal.

SUMMARY OF THE INVENTION

Accordingly, it is the object of the present invention to provide a pressure support system and method of providing a flow of breathing gas to a patient using an improved pressure generator and impeller design that overcomes the aforementioned shortcomings of conventional pressure support systems. It is a further object of the present invention to provide an improved impeller, a pressure generator using such an impeller, and a pressure generating system and method using such a pressure generator that overcomes the aforementioned shortcomings of conventional pressure support systems using conventional blower designs. It is a further object of the present invention to provide a pressure support system and method with an improved impeller configuration that provides a substantially constant pressure output over a range of flow rates typically associated with pressure support therapy. It is a further object of the present invention to provide a pressure support system and method with an improved impeller configuration that minimizes or eliminates the need for feedback control of the impeller in a pressure support system. A further object of the present invention is to provide an efficient blower and impeller design for use in respiratory support and other systems requiring a flow of gas.

These objects are achieved according to one embodiment of the present invention by providing a pressure generator that includes a housing having a gas inlet and a gas outlet, a motor, a rotatable drive shaft driven by the motor, and an impeller mounted on the drive shaft and disposed within the housing. The impeller includes a hub attached to the drive shaft, an impeller body attached to the hub extending radially from the hub to a perimeter of the impeller, and a plurality of impeller blades disposed on one face of the impeller body. Each impeller blade extends from a leading end of the blade, generally adjacent the hub, toward a trailing end of the blade, generally at the perimeter of the impeller. An inlet area is defined between each pair of adjacent blades generally adjacent the hub. Each inlet area is defined as the area at the radius of the leading end of the adjacent blades bounded by a height of the leading end of the adjacent blades and the one face of the impeller body. In addition, an outlet area is defined between each pair of adjacent blades generally adjacent the perimeter of the impeller. Each outlet area is defined as the area at the radius of the trailing end of the adjacent blades bounded by the height of the trailing end of the adjacent blades and the one face of the impeller body. Each inlet area is substantially equal to each corresponding outlet area for each pair of adjacent blades.

These objects are also achieved according to the present invention by providing a pressure support system and method of providing a flow of breathing gas that includes a source of breathing gas, a pressure generator, and a patient circuit coupled to the pressure generator for delivering the flow of breathing gas from the pressure generator to an airway of the patient. The pressure generator includes a motor, a rotatable drive shaft driven by the motor, and an impeller mounted on the drive shaft. The impeller is configured and arranged such that the pressure generator delivers a substantially constant pressure over a range of flows output from the pressure generator, including flows in the range of 10-150 l/min. In addition, the pressure generator delivers the substantially constant pressure selected over a range of pressures, including pressures in over a range of 10-65 $cmH_2O$, which is established based on a rotational speed of the motor.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
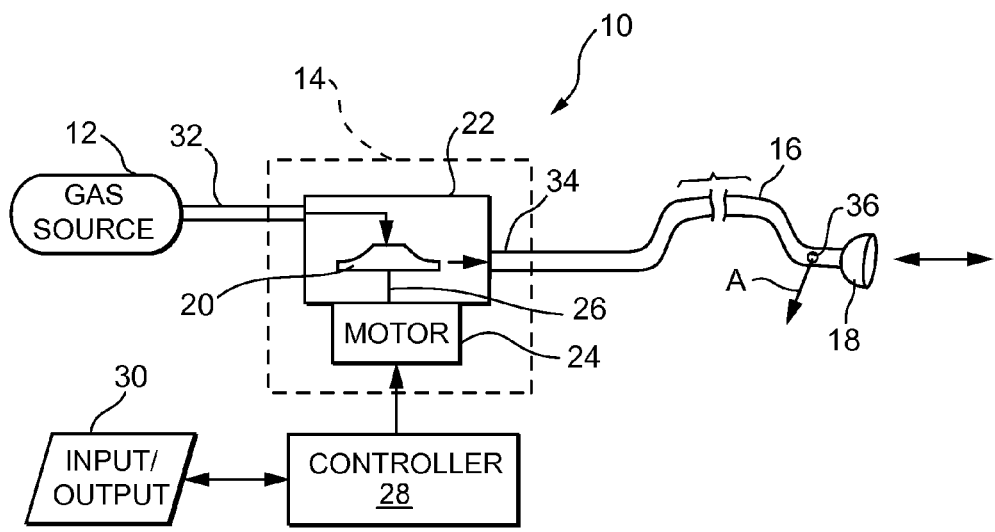
FIG. 1 is a schematic view of a pressure support system according to the principles of the present invention.

FIG. 1 schematically illustrates a pressure support system 10 according to the principles of the present invention. Pressure support system 10 includes a source of breathing gas 12, such as air from the ambient atmosphere or a tank, oxygen from a tank or oxygen concentrator, a mixture of gases, with or without nebulized medication or the like, as known in the art. Pressure support system 10 also includes a pressure generator 14 that receives gas from the gas source and elevates the pressure of the gas to produce a flow of breathing gas at a pressure that is greater than the ambient, i.e., atmospheric, pressure. A patient circuit 16, which is typically a flexible conduit, carries the pressurized flow of breathing gas to the patient. A patient interface device 18 coupled to the patient circuit communicates the flow of breathing gas from patient circuit 14 to the airway of the patient. Patient interface device 18 is any device suited for this purpose, such as a nasal mask, nasal/oral mask, total face mask, nasal cannula, trachea tube, endotracheal tube, hood, or other conventional patient respiratory gas delivery system as known in the art.

Pressure generator 14 includes an impeller 20 disposed within a housing 22. The details of impeller 20 are discussed below with reference to FIGS. 2-4, and the details of housing 22 are discussed below with reference to FIGS. 5-6. A motor 24 coupled to a drive shaft 26 rotates impeller 20. The operation of motor 24 is controlled by a controller 28. Controller 28 is any device, system or assembly suitable to operate motor 24. In its simplest form, controller 28 can be a power supply operated by an on/off switch. Of course, this allows for little control over the speed of motor 24. In a preferred embodiment of the present invention, controller 28 is capable of adjusting the speed of motor 24 to set the desired pressure to be output by pressure generator 14. To this end, conventional controls, which are schematically illustrated as input/output device 30, are provided for providing inputs to controller 28, for example to select the desired output pressure, and, hence, the operating speed of motor 24. Of course, the present invention also contemplates using input/output device 30 and controller 28 to control the operation of pressure support system 10, which can include setting and displaying information, such as current pressure settings, alarms, and usage of the system. Exemplary controls include an on/off control for the pressure support system, a timing type control for selective operation of the pressure support system 10, selectors for the desired pressures to be delivered by the pressure support system 10 and other controls and displays as known in the art.

Pressure generator 14 receives breathing gas from gas source 12 at a gas inlet 32 and elevates the pressure of the received gas. The flow of breathing gas having an elevated pressure is output at a gas outlet 34. In the illustrated embodiment, the output flow of breathing gas is delivered to patient circuit 16 for delivery to the patient via patient interface 18. In this embodiment, which illustrates a single-limb patient circuit, patient circuit 16 includes an exhaust vent 36 proximate to patient interface device 18. Exhaust vent 36 allows exhaled gases from the patient to vent to atmosphere as indicated by arrow A.

Figure 2:
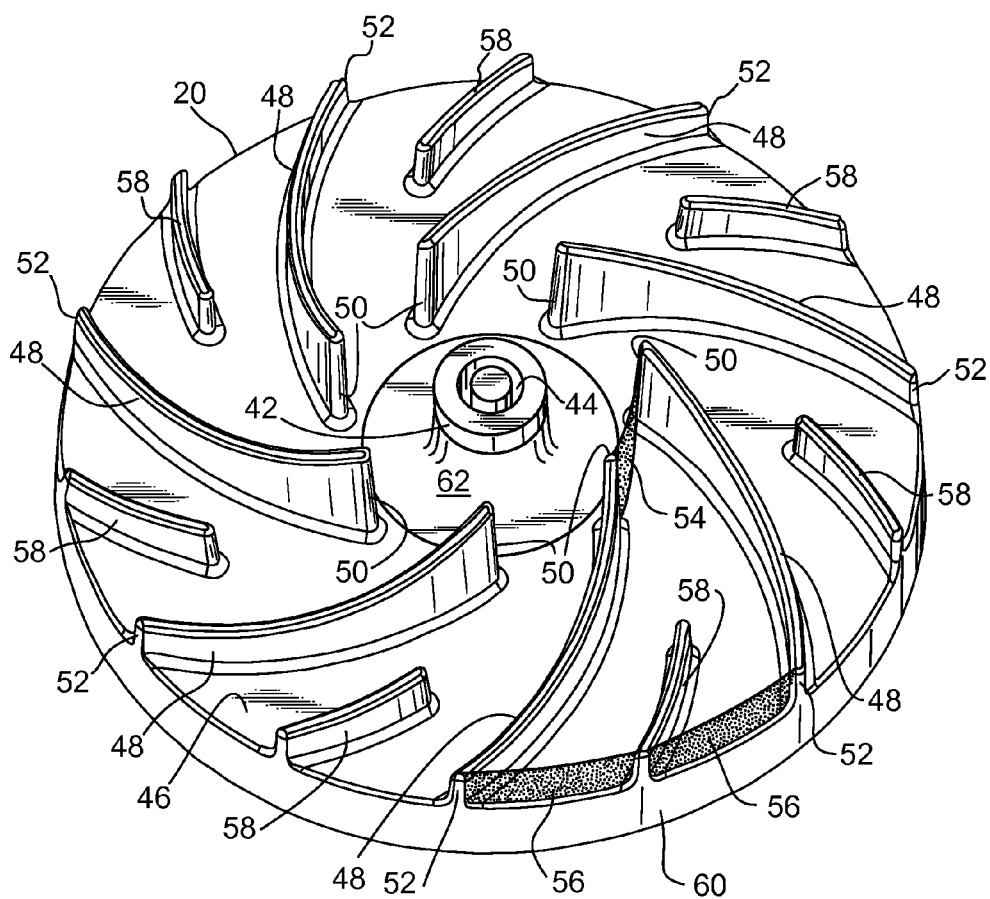
FIG. 2 is a perspective view of an impeller for use in the pressure support system of FIG. 1.
Figure 3:
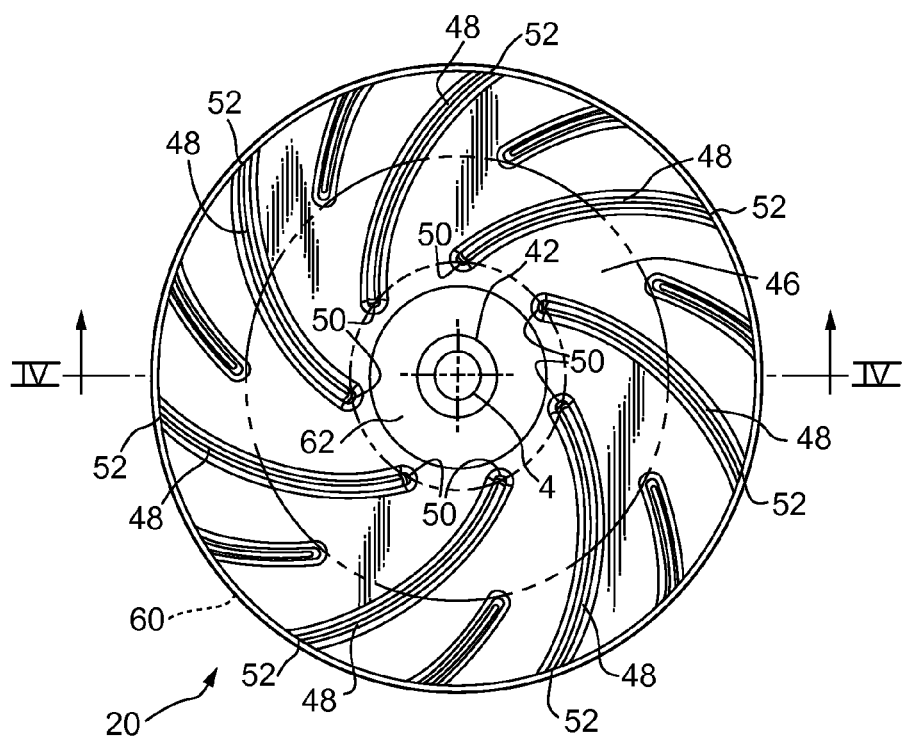
FIG. 3 is a top plan view of the impeller of FIG. 2.
Figure 4:
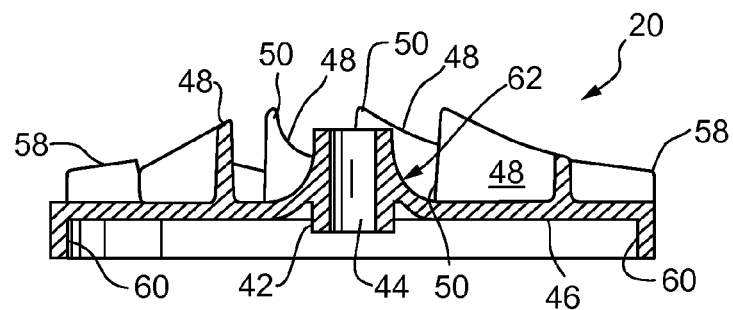
FIG. 4 is a cross-sectional view of the impeller of FIGS. 2 and 3 taken along line IV-IV of FIG. 3.

As shown in FIGS. 2-4, impeller 20 includes a hub 42 with a bore 44 therethrough so that the hub and impeller can receive drive shaft 26 and be attached thereto in a conventional fashion. Impeller 20 includes an impeller body 46 attached to hub 42 and extending generally radially from hub 42 to a perimeter of impeller 20. Impeller 20 includes a plurality of backward curved impeller blades 48 attached to an upper face of impeller body 46. Each blade 48 extends from a leading end 50, positioned generally adjacent hub 42, to a trailing end 52 at a perimeter of the impeller 40.

Blades 48 are designed for delivering a substantially constant pressure gas to gas outlet 34 even if the rate of flow of gas in the patient circuit varies. This aspect of the present invention is achieved, at least in part, by the shape and geometry of blades 48. Specifically, blades 48 define a plurality of inlet areas generally adjacent hub 42 and a plurality of outlet areas located generally adjacent the perimeter of impeller 20. One such inlet area 54 and outlet area 56 are illustrated in FIG. 2 with the illustrated outlet area 56 corresponding to the illustrated inlet area 54. The corresponding inlet and outlet areas are those inlet and outlet areas defined between the same adjacent blades 48. Each inlet area is defined as the area at the radius of leading end 50 of adjacent blades 48 bounded by a height of the leading end of the adjacent blades and the surface of impeller body 46. Each outlet area is defined as the area at the radius of the trailing end 52 of the adjacent blades 48 bounded by the height of the trailing end of the adjacent blades and the surface of the impeller body.

In the impeller body 46 of the present invention, each inlet area is substantially equal to each corresponding outlet area. Maintaining of the inlet area substantially equal to the outlet area is believed to provide a substantially constant pressure gas at the outlet 34, despite fluctuations in the flow rate typically encountered in a pressure support system. In the present invention, the outlet area is maintained substantially equal to the inlet areas by having blades 48 decrease in height as the blades extend radially outward from the hub 42. It is to be understood, however, that there are other techniques for maintaining each inlet area equal to the corresponding outlet area, other than decreasing the height of impeller blades 48. For example, using constant height blades, a portion of the outlet could be blocked having the resulting inlet and outlet areas be substantially equal. In the illustrated embodiment, a radial area between adjacent blades, which is an area between adjacent blades at a radial position from the hub and that is bounded by the height of the adjacent blades at the radial position and the one face of the impeller body, is substantially the same over a length of the pair of adjacent blades. Thus, for each pair of blades, each radial position along the length of the blades has substantially the same area.

Pressure generator 14 includes a means for minimizing the noise of the impeller 20. The noise minimizing means includes a plurality of partial blades 58 attached to the upper face of impeller body 46, with each partial blade 58 being disposed between a pair of adjacent blades 48. Each partial blade 58 extends from a position radially outward from inlet areas 54 about the midpoint of impeller body 46 to the perimeter of impeller 20. Partial blades 58 act on the flow of gas to minimize the noise created by impeller 20 during operation.

Impeller 20 is preferably a one-piece, injection molded, thermoplastic member. Of course, impeller 20 can be made from multiple components. For smooth operation of impeller 20, the impeller must be balanced. Conventional balancing of impellers and wheels, in general, requires that material be added to or deleted from the wheel typically at the perimeter of the structure. Impeller 20 of the present invention includes a balancing means to simplify the balancing operation. The balancing means includes an annular skirt 60 attached to impeller body 46 at the perimeter of impeller 20, with skirt 60 extending axially from the opposite face of impeller body 46 as blades 48 and partial blades 58. Skirt 60 provides a convenient location for removing selective material for balancing of impeller 20 without the removed material affecting the fluid flow in the impeller.

FIG. 4 additionally illustrates that hub 42 includes a smooth outer surface 62 curving radially outward toward inlet area 54. Smooth outer surface 62 is designed to guide the fluid flow from the gas inlet, which is centered above hub 42, to inlet areas 54 on the impeller 20 and further help minimize the noise associated with the operation of impeller 20.

Figure 5:
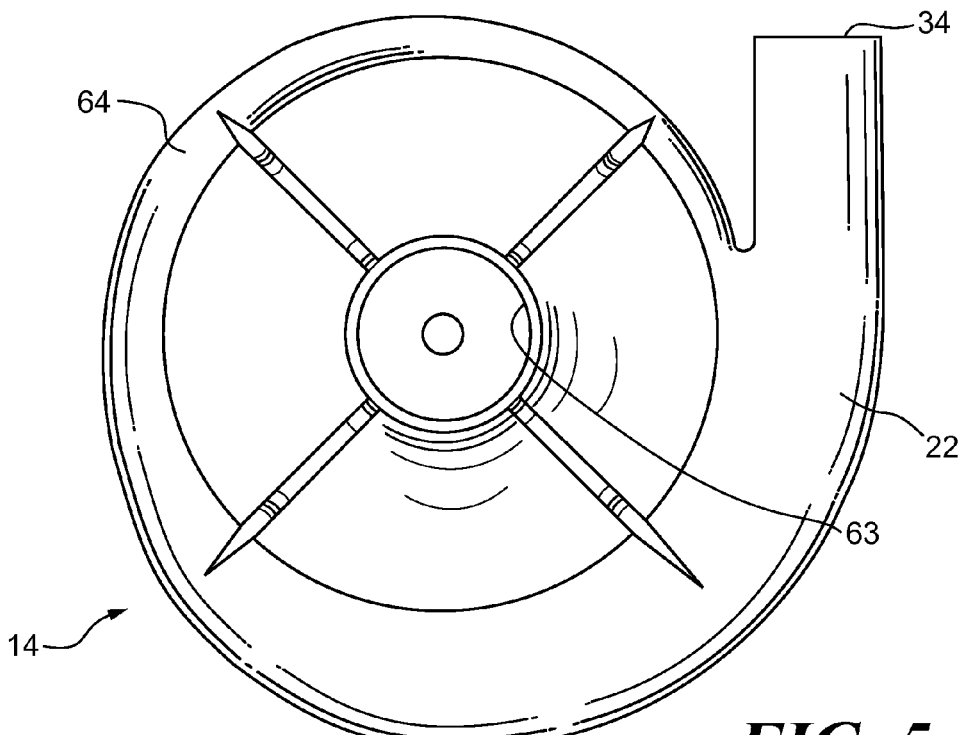
FIG. 5 is a top plan view of a pressure generator of the pressure support system of FIG. 1 including the impeller of FIGS. 2-4.
Figure 6:
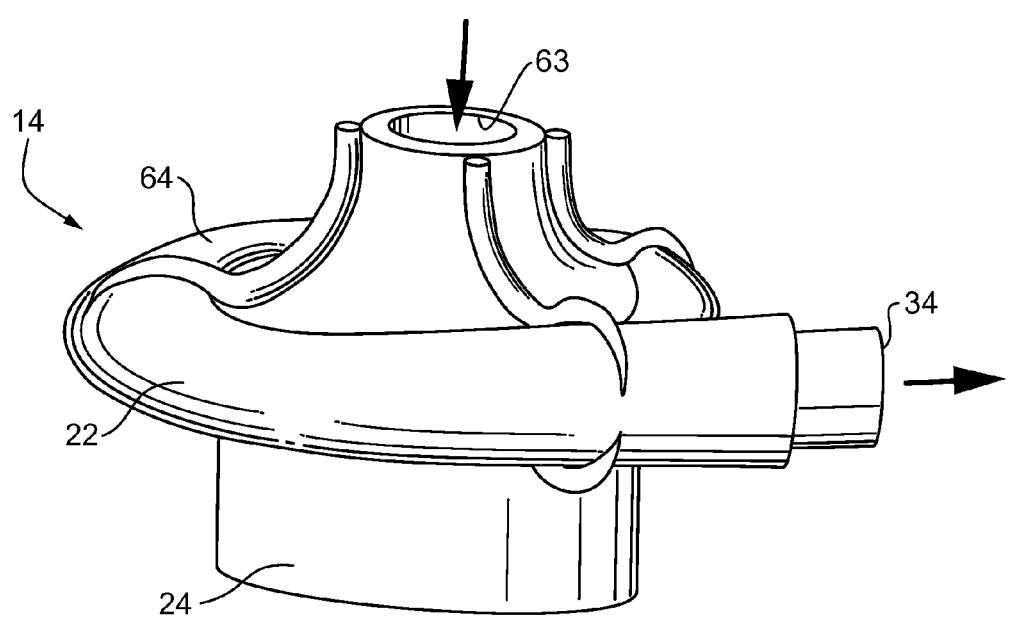
FIG. 6 is a perspective view of the pressure generator of FIG. 5.
Figure 7:
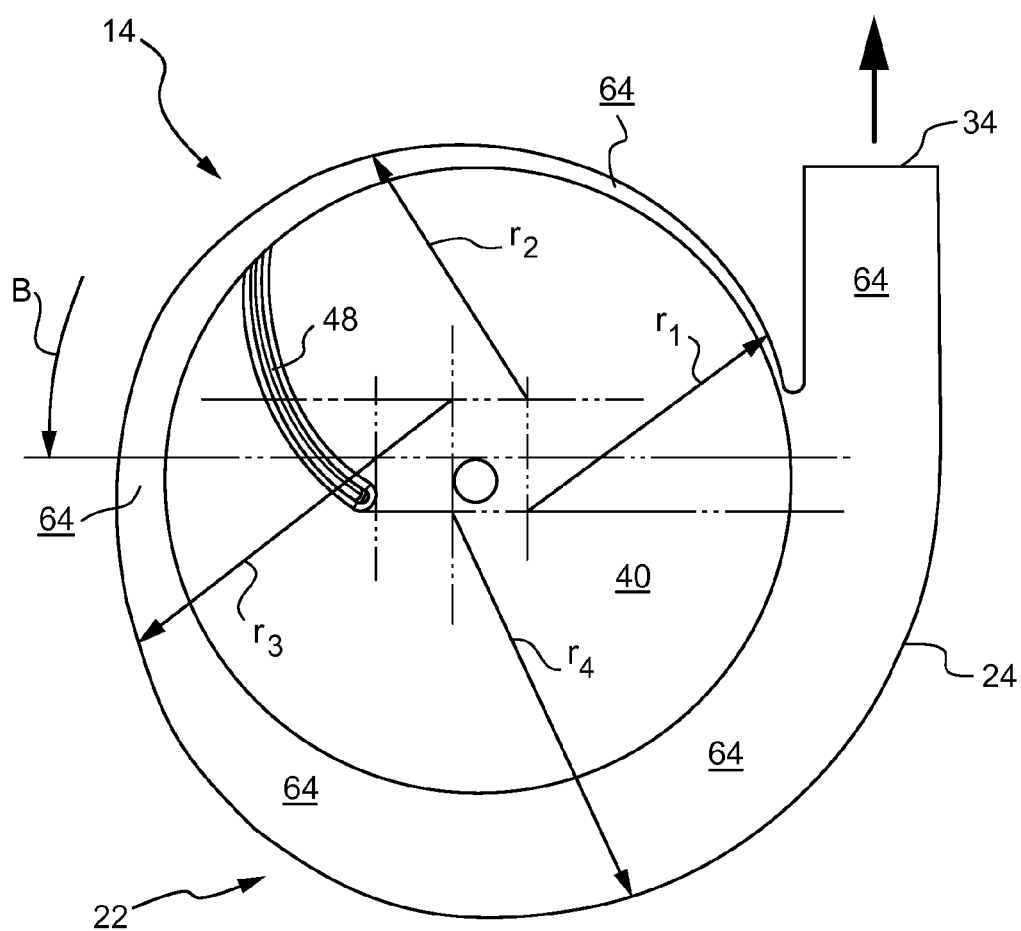
FIG. 7 is a schematic diagram of a pressure generator housing of the pressure generator of FIGS. 5 and 6.

Pressure generator 14 according to the present invention is shown in greater detail in FIGS. 5-7. As shown in FIGS. 5 and 6, housing 22 includes a gas flow inlet 63 located above the hub of the impeller so that gas enters housing 22 and is directed to the inlet areas of the impeller blades. As illustrated best in FIG. 6, housing 22 in pressure generator 14 follows the contour of the height of the blades 48 extending radially of impeller 20. Essentially, the gap between the upper portion of the individual blades 48 and housing 24 is minimized and is maintained constant along the length of blades 48. Conforming housing 24 to the shape of blades 48 is believed to further assist in maintaining a substantially constant pressure through conventional flow rates for respiratory therapy.

Additionally, as best shown in FIGS. 5-7, housing 22 includes a gas outlet channel 64 that extends circumferentially around impeller 20 and is provided with an arithmetically increasing cross-sectional area. The increasing cross-sectional area of the gas channel 64 results in an increased radius from leading end 50 of individual blades 48 to gas outlet channel 64 about the circumference of impeller 20. A single blade 48 and four respective radii $r_1$, $r_2$, $r_3$ and $r_4$ are illustrated in FIG. 7, with each radius extending from leading end 50 of a blade 48 to the outer perimeter of the gas outlet channel. As shown in FIG. 7, the radial distance $r_1$ through $r_4$ increases in a counter-clockwise direction as gas expelled from the trailing end of blades 48 moves through gas outlet channel 64 toward gas outlet 34 as indicated by arrow B.

The pressure support system of the present invention provides pressure support to a patient without the need for additional feedback control of the pressure generator in order to maintain a substantially constant outlet pressure. This is so because the pressure generator of the present invention, and, more specifically, the impeller shape and geometry allow the pressure generator to output a substantially constant pressure even if the flows in the patient circuit vary over a conventional range of flow rates associated with a pressure support system. In other words, the pressure generator of the present invention has a substantially flat pressure curve over the desired operating range. In this manner, the pressure generator of the present invention has greater efficiency than conventional pressure generators, which allows for a relatively smaller power design, longer battery life in a portable pressure generating system, with less heat generation and subsequent noise reduction.

The design of the individual blades 48 on impeller 20 provides a smooth output pressure that also results in increased patient comfort. Another advantage of the substantially flat pressure curve is that flow in the patient circuit can be determined as a direct function of motor current or PWM duty cycle. This characteristic allows pressure support system 10 to be designed without conventional flow sensors and the associated operational amplified circuitry.

Figure 8:
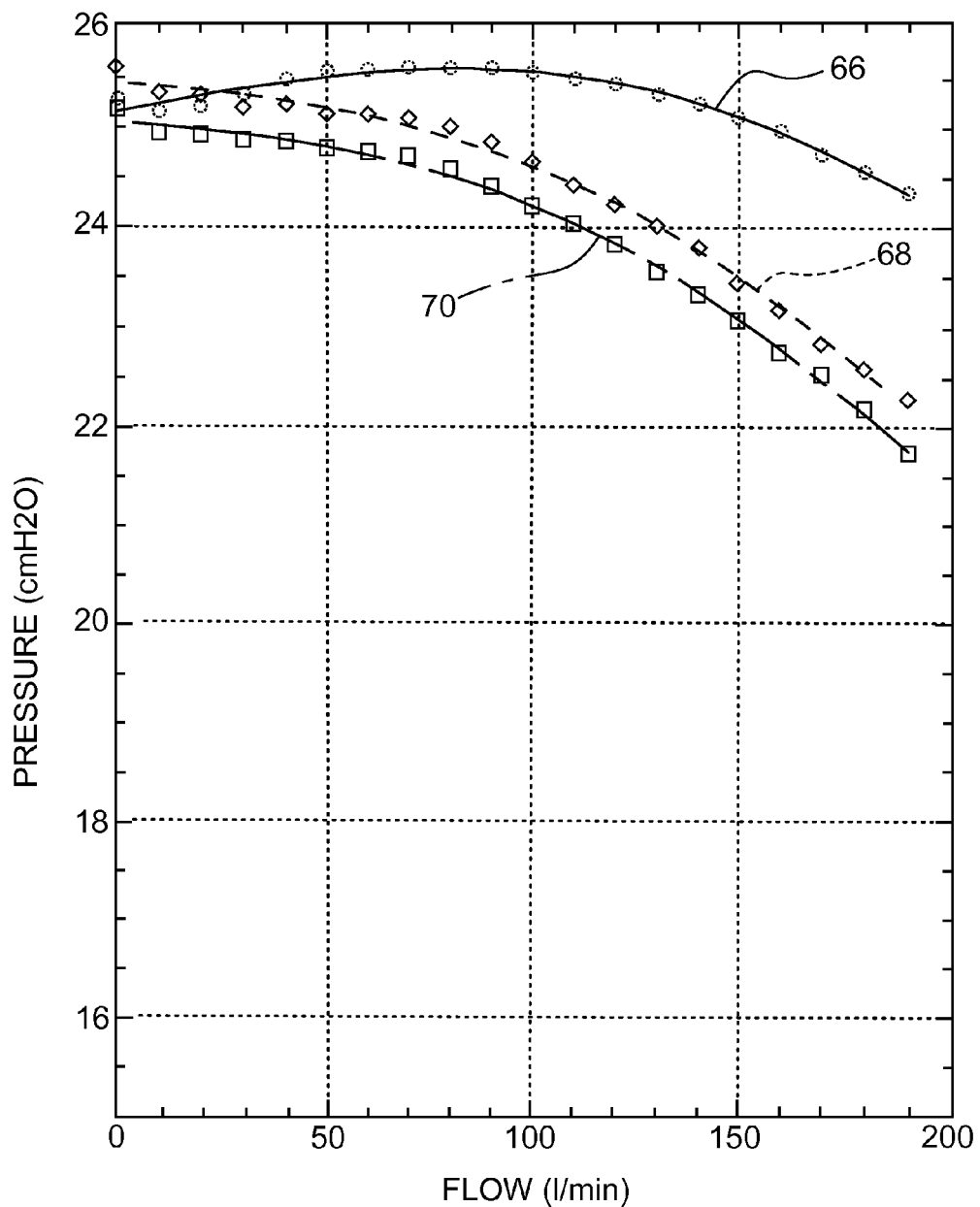
FIG. 8 is a chart of the output pressure of the pressure generator according to the present invention compared to the conventional pressure generators over conventional pressure support therapy flow rates.

FIG. 8 is a chart illustrating a pressure curve 66 output by pressure generator 14 according to the present invention as compared to pressure curves 68 and 70 of conventional blowers over conventional respiratory therapy flow rates. Specifically, FIG. 8 compares a pressure curve 66 of a seven blade impeller having a substantially equal inlet and outlet area according to the principles of the present invention versus pressure curves 68 and 70 of conventional nine blade impellers having 24 bdcm and 12 bdcm, respectively. All of the comparisons were done at the same motor speed. As can be seen from FIG. 8, impeller 20 provides a substantially constant pressure, which is ±1.0 cmH$_2$O of a selective constant pressure between 0 and 190 l/min representing a conventional range of respiratory therapy flow rates. Impeller 40 in this example provides a substantially constant pressure of about 25.25 cmH$_2$O with the variance being well within ±0.5 cmH$_2$O of the constant output pressure between 0 and 150 l/min. As illustrated, this represents a significantly more constant output pressure over the desired operating range than the conventional devices, which essentially decrease continuously throughout the desired operating range of flow rates. The illustrated conventional examples drop about 3 cmH$_2$O over 190 l/min flow conducted in the test.

Figure 9:
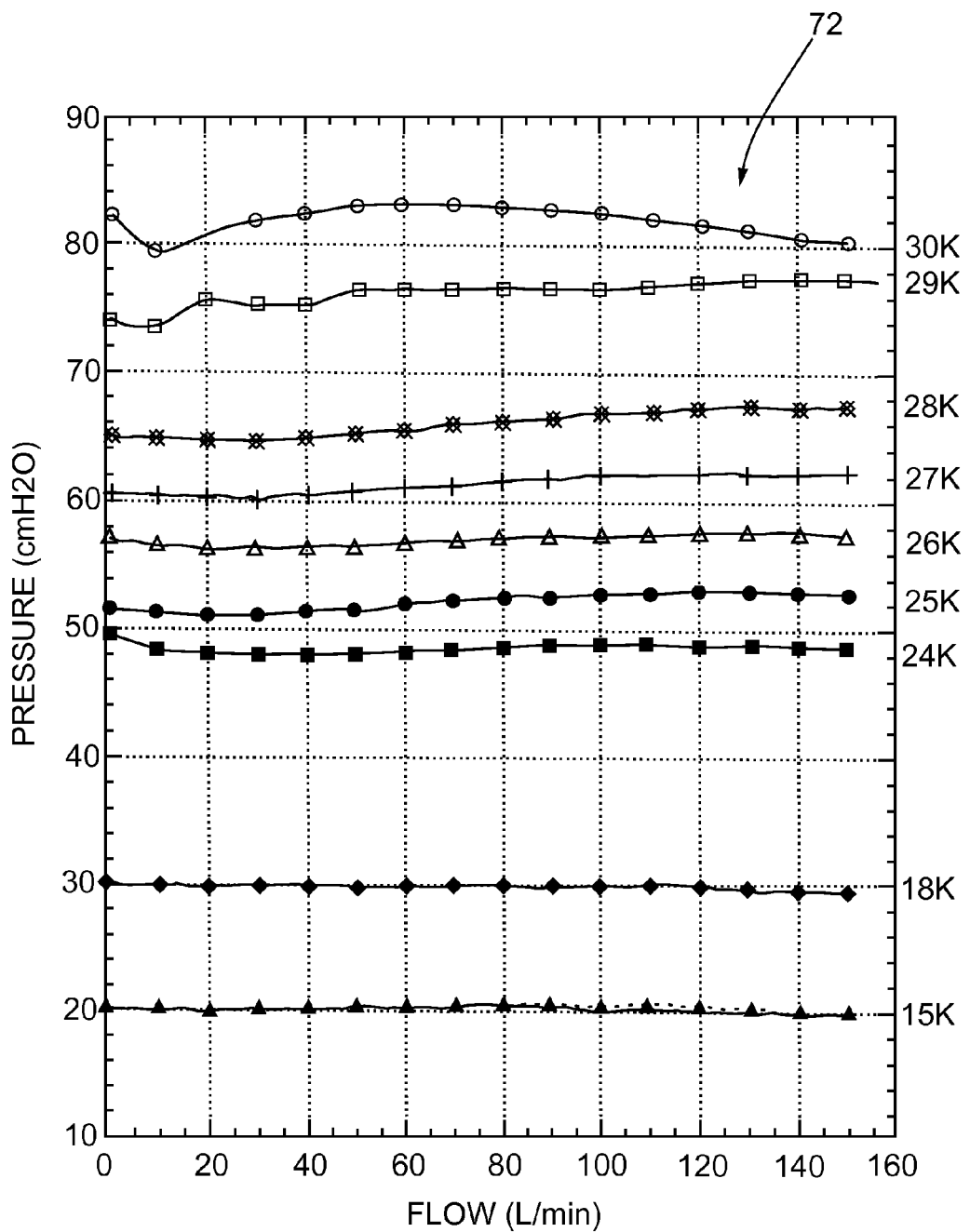
FIGS. 9 and 10 are charts illustrating the output pressure of the pressure generator of the present invention over conventional pressure support therapy flow rates and at a number of motor speeds.
Figure 10:
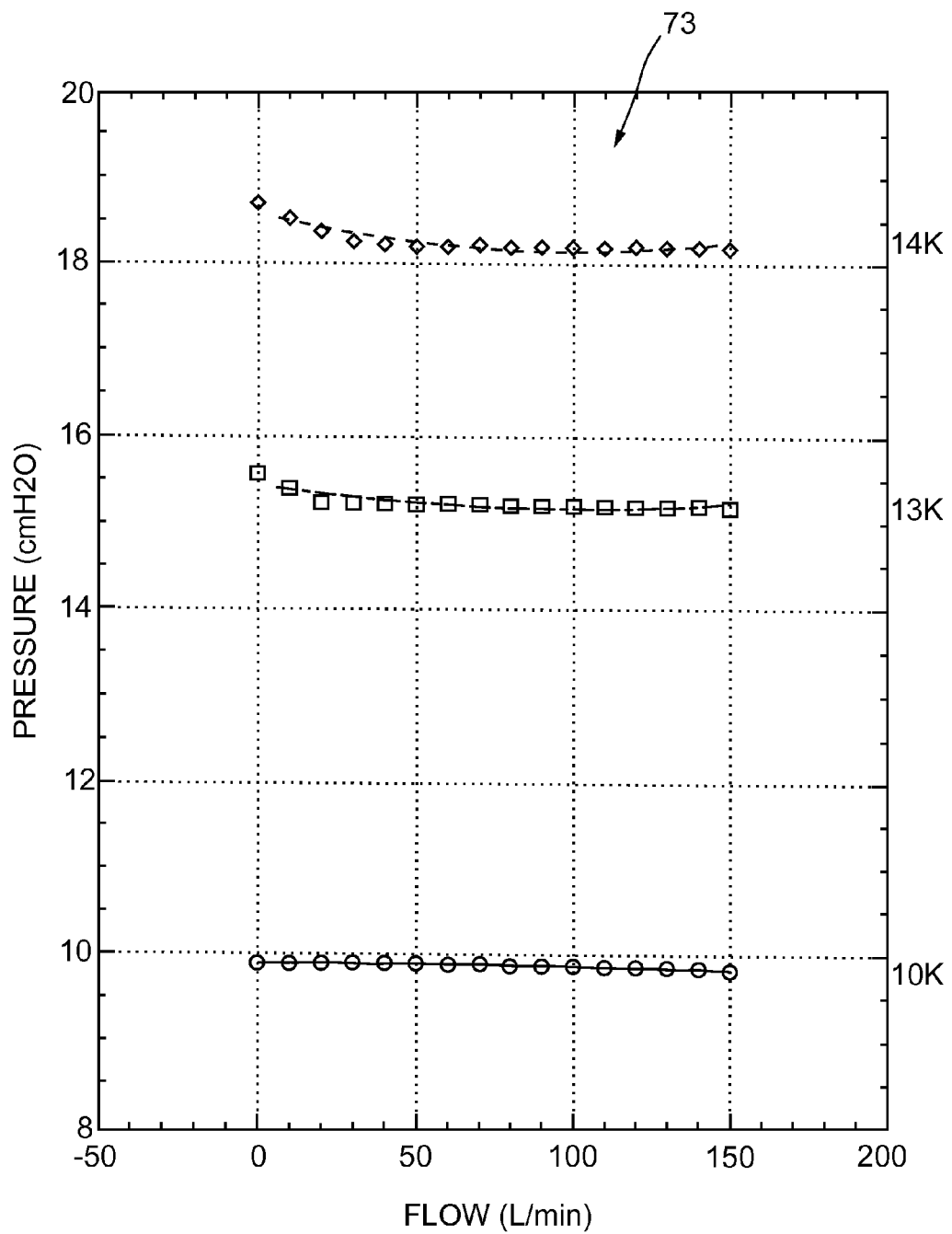

FIGS. 9 and 10 are charts illustrating a number of pressure curves 72 and 73 for the output pressure of the pressure generator of the present invention over conventional pressure support therapy flow rates, with each curve representing a different motor speed for motor 24. It is significant to note that pressure generator delivers a substantially constant pressure over a range of flow rates from approximately 10-150 l/min, where the output pressure covers a range of pressures, such as 10-65 cmH$_2$O. In particular, the pressure generator outputs a flow of breathing gas where the standard deviation from a selected pressure, i.e., a pressure in the range of pressures from 10-65 cmH$_2$O, is not greater than approximately 1.5 cmH$_2$O. Also, at a constant rotational speed, as the output flow increases, the pressure output by the pressure generator increases slightly over at least a portion of the range of flows from 10-150 l/min.

In the embodiments discussed above, the pressure support system delivers a flow of breathing gas at a selected pressure that remains constant over a range of flow variations in the patient circuit, which is essentially the function of a CPAP pressure support system. It is to be understood, however, that the impeller and pressure generator of the present invention are equally useful in system where the pressure of gas delivered to the patient is varied, either with the patient's breathing cycle or otherwise.

Figure 11:
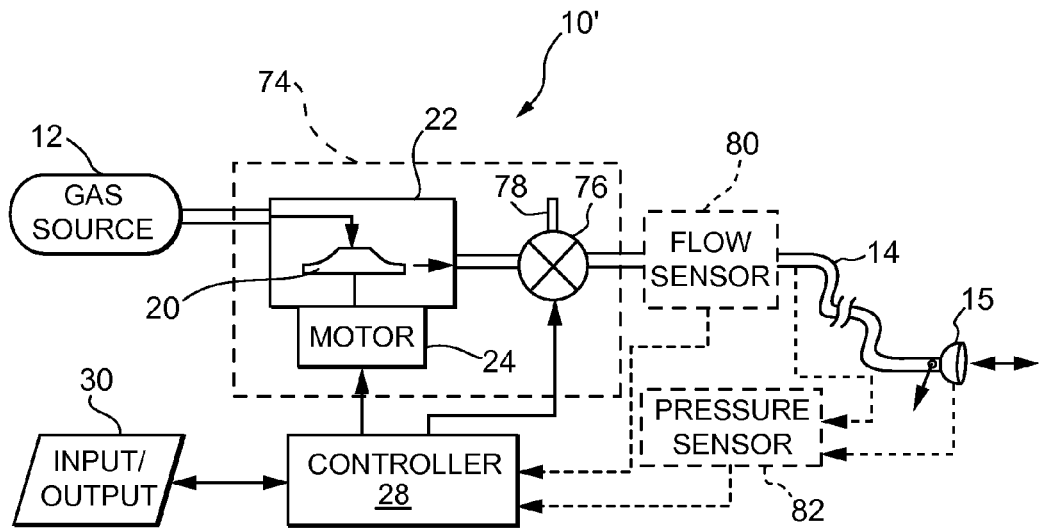
FIG. 11 is a schematic view of a pressure support system according to another embodiment of the present invention.

FIG. 11 is a schematic view of a pressure support system 10' according to another embodiment of the present invention that is capable of varying the pressure of the flow of breathing gas and that uses impeller 20 discussed above. Pressure support system 10' is essentially the same as pressure support system 10 except for the inclusion of components used to control the pressure output by pressure generator 74. For example, in the embodiment illustrated in FIG. 11, a flow control valve 76 is provided downstream of impeller 20 to exhaust a portion of the flow of gas via an exhaust vent 78, thereby controlling the pressure or flow delivered to the patient. A flow sensor 80 and/or pressure sensor 82 associated with the patient circuit and/or patient interface provide the feedback information for achieving the desired pressure. The output of the sensors 80 and 82 are provided to controller that controls motor 24 and/or valve 76 for providing the selected pressure to the patient.

Because the impeller of the present invention is used in pressure generator 74 of this embodiment, it is not necessary to use the feedback function of sensors 80 or 82 as a micro-control type of system to ensure that the pressure generator maintains the selected pressure. Instead, the present invention contemplates that this type of pressure control is used as a macro-control to achieve the selected pressure. For example, in a bi-level pressure support the output pressure alternates between an inspiratory positive airway pressure (IPAP) and a lower expiratory positive airway pressure (EPAP). The flow control components, i.e., sensors 80 and/or 82 and valve 76, are used to alternate between these two pressure levels (macro control). They are not used to ensure that the IPAP or EPAP is maintained at the desired level (micro control).

It is to be understood a number of possible configurations are possible for the pressure support system depending, for example, on its level of complexity and intended use. For example, an auto-titration type pressure support system would include appropriate sensors and pressure/flow control elements for adjusting the pressure provided to the patient as needed in implementing the auto-titration algorithm. In addition, valve 76 can be provided upstream of impeller 20 to control the flow of gas to the impeller. In addition, sensors 80 and 82 can be eliminated in favor of other techniques for measuring a parameter associated with the flow of breathing gas in the pressure support system.

While the impeller of the present invention has been described above with respect to a medical device, in particular, a pressure support system, it is to be understood that it is also useful in other applications and is not intended to be specifically limited to medical applications. On the contrary, the impeller and pressure generator of the present invention can be used in any system where a flow of gas is to be provided.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support system, comprising:
    a source of gas;
    a patient circuit; and
    a pressure generator coupled to the source of gas and the patient circuit, the pressure generator including:
        (a) a housing having a gas inlet and a gas outlet;
        (b) a motor;
        (c) a rotatable drive shaft driven by the motor; and
        (d) an impeller mounted on the drive shaft and disposed within the housing, the impeller comprising:
            (1) a hub attached to the drive shaft,
            (2) an impeller body attached to the hub extending radially from the hub to a perimeter of the impeller,
            (3) a plurality of impeller blades disposed on one face of the impeller body, each impeller blade extending from a leading end of the blade generally adjacent the hub toward a trailing end of the blade generally at the perimeter of the impeller, wherein the plurality of impeller blades decrease in height from the leading end to the trailing end, wherein an inlet area is defined between each pair of adjacent blades generally adjacent the hub, with each inlet area being defined as the area at the radius of the leading end of the adjacent blades bounded by a height of the leading end of the adjacent blades and the one face of the impeller body, and wherein an outlet area is defined between each pair of adjacent blades generally adjacent the perimeter of the impeller, with each outlet area being defined as the area at the radius of the trailing end of the adjacent blades bounded by the height of the trailing end of the adjacent blades and the one face of the impeller body, wherein each inlet area is substantially equal to each corresponding outlet area for each pair of adjacent blades;
    wherein the pressure generator receives gas from the source of gas and, based on a preselected pressure of between 10-65 cmH$_2$O and -responsive to and despite fluctuations in a rate of flow of gas in the patient circuit over a range of 10-150 l/min, outputs a flow of breathing gas having a pressure within a standard deviation of no more than 1.5 cmH$_2$O of the preselected pressure using a constant, selected operating speed of the motor selected based on the preselected pressure and without feedback control based on either or both of a pressure in the patient circuit or a flow rate in the patient circuit.

2. The pressure support system of claim 1, the impeller further comprising a plurality of partial blades disposed on the one face of the impeller body, wherein each partial blade is positioned between a respective pair of adjacent impeller blades and extends from a position radially outward of the inlet area defined between the adjacent impeller blades to the perimeter of the impeller, wherein each partial blade extends from a midpoint of the one face of the impeller body between the adjacent impeller blades to the perimeter of the impeller.

3. The pressure support system of claim 1, wherein the blades are backward curved blades.

4. The pressure support system of claim 1, wherein the hub includes a smooth outer surface curving radially outwardly toward the plurality of inlet areas.

5. The pressure support system of claim 1, wherein the housing outlet has an arithmetically increasing cross sectional area extending at least partially around the perimeter of the impeller.

6. The pressure support system of claim 1, wherein the housing follows the contour of the height of the blades.

7. The pressure support system of claim 1, wherein a radial area between adjacent blades, which is an area between adjacent blades at a radial position from the hub and that is bounded by the height of the adjacent blades at the radial position and the one face of the impeller body, is substantially the same over a length of the pair of adjacent blades.

8. A method of supplying a flow of gas to a patient circuit, comprising:
    (a) providing a source of gas;
    (b) providing a pressure generating system comprising:
        (1) a housing having a gas inlet and a gas outlet,
        (2) a motor,
        (3) a rotatable drive shaft driven by the motor, and
        (4) an impeller mounted on the drive shaft and disposed within the housing, the impeller comprising:
            (i) a hub attached to the drive shaft,
            (i) an impeller body attached to the hub extending radially from the hub to a perimeter of the impeller,
            (iii) a plurality of impeller blades disposed on one face of the impeller body, each impeller blade extending from a leading end of the blade generally adjacent the hub toward a trailing end of the blade generally at the perimeter of the impeller, wherein the plurality of impeller blades decrease in height from the leading end to the trailing end, wherein an inlet area is defined between each pair of adjacent blades generally adjacent the hub, with each inlet area being defined as the area at the radius of the leading end of the adjacent blades bounded by a height of the leading end of the adjacent blades and the one face of the impeller body, and wherein an outlet area is defined between each pair of adjacent blades generally adjacent the perimeter of the impeller, with each outlet area being defined as the area at the radius of the trailing end of the adjacent blades bounded by the height of the trailing end of the adjacent blades and the one face of the impeller body, wherein each inlet area is substantially equal to each corresponding outlet area for each pair of adjacent blades;
    (c) receiving gas from the source of gas in the pressure generating system and, based on a preselected pressure of between 10-65 cmH$_2$O and -responsive to and despite fluctuations in a rate of flow of gas in the patient circuit over a range of 10-150 l/min, outputting from the pressure generating system a flow of breathing gas having a pressure within a standard deviation of no more than 1.5 cmH$_2$O of the preselected pressure using a constant, selected operating speed of the motor selected based on the preselected pressure and without feedback control based on either or both of a pressure in the patient circuit or a flow rate in the patient circuit; and (d) delivering the pressurized gas to the patient circuit, the patient circuit being coupled to the gas outlet of the housing.

9. The method of claim 8, the impeller further comprising a plurality of partial blades disposed on the one face of the impeller body, wherein each partial blade is positioned between a respective pair of adjacent impeller blades and extends from a position radially outward of the inlet area defined between the adjacent impeller blades to the perimeter of the impeller.

10. The method of claim 8, the impeller further comprising a skirt extending around the perimeter of the impeller, the skirt extending downwardly from a second face of the impeller body opposite the one face of the impeller body.

11. A method of supplying gas comprising:
(a) providing a source of breathing gas;
(b) providing a pressure generator comprising:
 (1) a motor,
 (2) a rotatable drive shaft driven by the motor, and
 (3) an impeller mounted on the drive shaft;
(c) providing a patient circuit;
(d) receiving gas from the source of breathing gas in the pressure generator and , based on a preselected pressure of between 10-65 cmH$_2$O and -responsive to and despite fluctuations in a rate of flow of gas in the patient circuit over a range of 10-150 l/min, outputting from the pressure generator a flow of breathing gas having a pressure within a standard deviation of no more than 1.5 cmH$_2$O of the preselected pressure using a constant, selected operating speed of the motor selected based on the preselected pressure and without feedback control based on either or both of a pressure in the patient circuit or a flow rate in the patient circuit; and
(d) supplying the pressurized gas from the pressure generator to the patient through the patient circuit.

12. The method of claim 11, wherein pressuring the gas includes outputting the flow of breathing gas such, at a constant rotational speed, as the output flow increases, the pressure of the flow of breathing is greater than the preselected pressure over at least a portion of the range of flows from 10-150 l/min.

* * * * *